(12) United States Patent
Pritchard et al.

(10) Patent No.: US 7,482,362 B2
(45) Date of Patent: Jan. 27, 2009

(54) SUBSTITUTED-4-QUINOLONES

(75) Inventors: David Idris Pritchard, Barrow Upon Soar (GB); Barrie Walsham Bycroft, Besston (GB); Siri Ram Chhabra, Leicester (GB); Doreen Hooi, Nottingham (GB)

(73) Assignee: The Secretary of State for Defense, Salisbury, Wiltshire (GB)

( * ) Notice: Subject to any disclaimer, the term of this patent is extended or adjusted under 35 U.S.C. 154(b) by 698 days.

(21) Appl. No.: 10/450,930

(22) PCT Filed: Dec. 17, 2001

(86) PCT No.: PCT/GB01/05550

§ 371 (c)(1),
(2), (4) Date: Dec. 1, 2003

(87) PCT Pub. No.: WO02/47686

PCT Pub. Date: Jun. 20, 2002

(65) Prior Publication Data

US 2004/0082579 A1 Apr. 29, 2004

(30) Foreign Application Priority Data

Dec. 16, 2000 (GB) ................... 0030729.8

(51) Int. Cl.
*A01N 43/42* (2006.01)
*A61K 31/47* (2006.01)
*C07D 215/00* (2006.01)

(52) U.S. Cl. ...................... 514/311; 546/153
(58) Field of Classification Search ................. 514/311; 546/153
See application file for complete search history.

(56) References Cited

U.S. PATENT DOCUMENTS 6,150,326 A * 11/2000 Golovistikov et al. .......... 514/8

FOREIGN PATENT DOCUMENTS

| EP | 0361177 | 4/1990 |
| JP | 11092307 | 4/1999 |
| WO | WO 9817662 | 4/1998 |

OTHER PUBLICATIONS

Abe, M; Ishikawa, O.; and Miyachi, Y., "Changes in peripheral blood lymphocyte subsets during cyclosporin administration in patients with psoriasis vulgaris", Sep. 1997, European Journal of Dermatology, vol. 7, No. 6, pp. 417-420.*

* cited by examiner

*Primary Examiner*—Sreeni Padmanabhan
*Assistant Examiner*—Kendra D Carter
(74) *Attorney, Agent, or Firm*—Bozicevic, Field & Francis, LLP; Bret E. Field

(57) ABSTRACT

Substituted-4-quinolones of the formula (I): wherein $R^1$ is a straight or branched chain, saturated or ethylenically-unsaturated aliphatic hydrocarbyl group containing 1 to 18 carbon atoms which may optionally be substituted by one or more substituent groups selected from halo, 1-6C alkoxy, carboxy, 1-6C alkoxycarbonyl and $NR^6R^7$, wherein each of $R^6$ and $R^7$ is independently selected from H and 1-6C alkyl or $R^6$ and $R^7$ together with the N atom to which they are attached form a saturated heterocyclic group selected from piperidino, piperazino and morpholino; $R^2$ is a group selected from H, —OH, halo, —CHO, —$CO_2$H and $CONHR^8$ wherein $R^8$ is H or a 1-6C alkyl; each of $R^3$, $R^4$ and $R^5$ is independently selected form H, —$CH_3$, —$OCH_3$ and halo; or a non-toxic pharmaceutically-acceptable salt thereof, have use in the manufacture of a medicament for the treatment of a disease of a living animal body, including a human, which disease is responsive to the activity of an immunosuppressant. The preferred compound of the formula 1 is 2-n-heptyl-3-hydroxy-4(1H)-quinolone.

9 Claims, 3 Drawing Sheets

Figure 1:
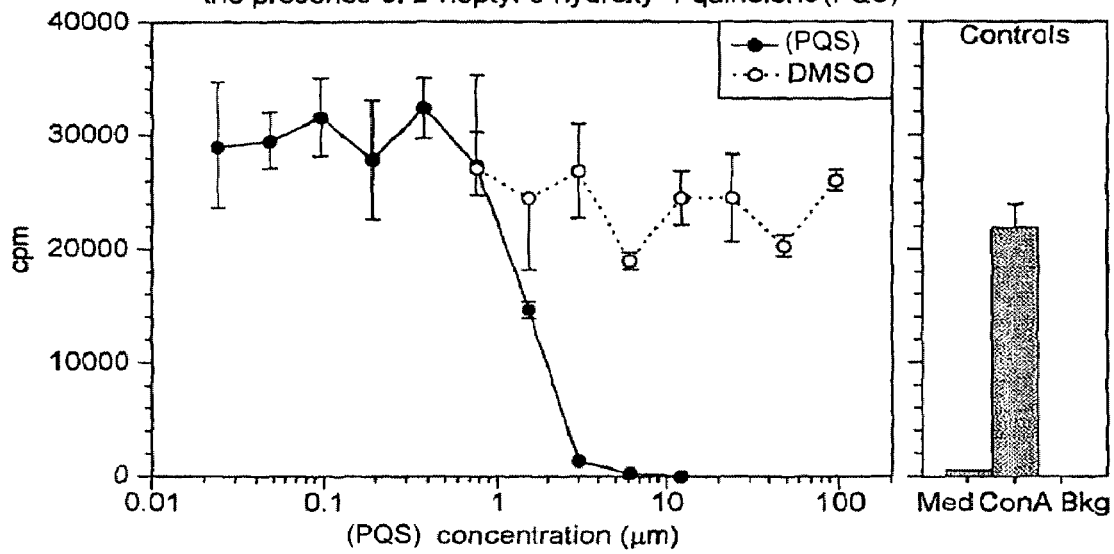

Proliferation of Balb/C Splenocytes stimulated with ConA in the presence of 2-heptyl-3-hydroxy-4-quinolone (PQS)

The viability of the human monocytic cell line, Mono Mac 6, was not affected by PQS in contrast to other bacterial quorum sensing molecule, OdDHL, when assessed by the bioreduction of MTS.

The differential effects of bacterial quorum sensing molecules on *in vitro* assays of human peripheral blood mononuclear cells when stimulated with the lectin Concanavalin A for the release of IL-2 and the induction of cell proliferation, and the production of TNF-$\alpha$ in the presence of LPS

SUBSTITUTED-4-QUINOLONES

The invention relates to substituted-4-quinolones which have immunosuppressant properties, to their use in the manufacture of medicaments and to a method of treating a disease responsive to the activity of an immunosuppressant using these quinolones.

Immunosuppressant compounds induce an inhibition of the immune response system. Compounds which are known to exhibit immunosuppressant activity include the fungal metabolite Cyclosporin A and the macrolide antibiotic (a metabolite from *Streptomyces tsukabaensis*) termed FK506. Both of these agents have been used clinically and experimentally to suppress the immune system in transplantation and in the treatment of a number of diseases.

Autoimmune diseases are disorders where the host discrimination of "self" versus "non-self" breaks down and the individual's immune system (both acquired and innate components) attacks self tissues. These diseases range from common entities such as rheumatoid arthritis, thyroid autoimmune disease and type 1 diabetes mellitus to less common entities such as multiple sclerosis and to rarer disorders such as myasthenia gravis. Advances in basic biomedical science and, in particular, in immunology have indicated that the main and fundamental lesion responsible for the induction and persistence of most autoimmune diseases resides within autoreactive proliferating T lymphocytes. In fact, the majority of autoimmune diseases are linked to a loss of T cell homeostasis. The healthy immune system is held in balanced equilibrium, apparently by the contra-suppressive production of cytokines by T helper 1 (Th1) and T helper 2 (Th2) lymphocyte subsets. In autoimmunity, Th1 cytokines predominate; in allergy, Th2 cytokines take their place. A cytokine intimately associated with the development of Th1 biased responses and, consequently, autoimmune disease is TNF-α.

Both Cyclosporin A and FK506 have been used clinically in the treatment of autoimmune diseases with encouraging results.

The currently available immunosuppressant drugs have the disadvantage of a narrow therapeutic index, i.e., toxicity versus clinical benefit. The compounds are known to be nephrotoxic, neurotoxic and potentially diabetogenic and this has limited their use in the fields mentioned above. Problems also exist with the administration of these compounds, their bioavailability and the monitoring of their levels both clinically and in the laboratory.

Experimental results obtained indicate that members of a particular class of substituted 4-quinolone compounds exhibit immunosuppressant activity.

According to one aspect, the present invention provides the use of a compound of the formula I

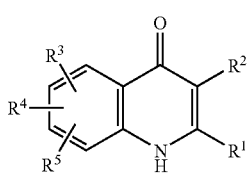

(I)

wherein $R^1$ is a straight or branched chain, saturated or ethylenically-unsaturated aliphatic hydrocarbyl group containing from 1 to 18 carbon atoms which may optionally be substituted by one or more substituent groups selected from halo, 1-6C alkoxy, carboxy, 1-6C alkoxycarbonyl and $NR^6R^7$, wherein each of $R^6$ and $R^7$ is independently selected from H and 1-6C alkyl or $R^6$ and $R^7$ together with the N atom to which they are attached form a saturated heterocyclic group selected from piperidino, piperazino and morpholino; $R^2$ is a group selected from H, —OH, halo, —CHO, —CO$_2$H and CONHR$^8$ wherein $R^8$ is H or a 1-6C alkyl; each of $R^3$, $R^4$ and $R^5$ is independently selected from H, —CH$_3$, —OCH$_3$ and halo; or a non-toxic pharmaceutically-acceptable salt thereof, for the manufacture of a medicament for the treatment of a disease of a living animal body, including a human, which disease is responsive to the activity of an immunosuppressant.

We believe that the compounds having the formula I as defined above, including non-toxic pharmaceutically-acceptable salts thereof, are capable of modulating the immune response in the living animal body, including human. In particular, we believe that these compounds have an inhibitory effect on lymphocyte proliferation in humans. The present invention, therefore, also provides a method of treating a disease of a living animal body, including a human, which disease is responsive to the activity of an immunosuppressant, e.g., an autoimmune disease, which method comprises administering to the living animal body, including human, a therapeutically-effective amount of a compound as described above.

The compounds having immunosuppressant properties have the general formula I given above and include their non-toxic pharmaceutically-acceptable salts. The group $R^1$ in formula I is a straight or branched chain 1 to 18C, preferably 3 to 13C, hydrocarbyl group which may be saturated or which may be ethenically unsaturated. This group may, optionally, be substituted by one or more substituents groups selected from halo, for example, F, Cl, Br or I; 1-6C alkoxy, for example methoxy, ethyoxy, n-propoxy, iso-propoxy, n-butoxy, isobutoxy and tert-butoxy; carboxy including non-toxic salts thereof; 1-6C alkoxycarbonyl, for example methoxycarbonyl; and NR$^6$R$^7$ wherein each of R$^6$ and R$^7$ is independently selected from H and 1-6C alkyl, for example methyl or ethyl. $R^6$ and $R^7$, together with the N atom to which they are attached may, alternatively, form a piperidino moiety, a morpholino moiety or a piperazino moiety in which the 4-N atom may, optionally, be substituted by a methyl group.

Typically, the hydrocarbyl group $R^1$ will be a straight chain alkyl group having from 3 to 13 carbon atoms, for example, propyl, n-pentyl, n-heptyl, n-nonyl and n-undecyl, which may optionally be substituted as described above. Preferably, in the formula I above the group $R^1$ will be n-heptyl.

The group $R^2$ is selected from H, —OH, halo, for example F, Cl, Br and I, CHO, CO$_2$H and CONHR$^8$ wherein R$^8$ is H or 1-6C alkyl. In the case where R$^2$ is a carboxylic acid group the scope of the invention includes the non-toxic metal and ammonium salts of the carboxylic acid. Preferably, however the group $R^2$ is OH. Each of the groups $R^3$, $R^4$ and $R^5$ is independently selected from H, CH$_3$, OCH$_3$ and halo, for example F, Cl, Br and I. Thus $R^3$, $R^4$ and $R^5$ may be the same or different groups. Any of the $R^3$, $R^4$ and $R^5$ groups may be attached to any of the free ring positions on the fused benzene ring of the quinolones, i.e., at ring positions 5, 6, 7 and 8. Preferably when not all of the $R^3$, $R^4$ and $R^5$ are H, substitution on the quinolone structure will be at position 6, 7 or both. More preferably, however, all of $R^3$, $R^4$ and $R^5$ are H, i.e., the fused benzene ring of the quinolone is unsubstituted.

An especially preferred compound having the formula I above for use in the present invention is 2-n-heptyl-3-hydroxy-4(1H)-quinolone.

As mentioned above, the compounds of formula I, and non-toxic salts thereof, have use as pharmaceutically active ingredients in the treatment of an animal body, including the human body, suffering from a disease or disorder which is responsive to the activity of an immunosuppressant, for instance for the treatment of an autoimmune disease, such as psoriasis, multiple sclerosis or rheumatoid arthritis. The dosage administered to the animal body in need of therapy will, of course, depend on the actual active compound used, the mode of treatment and the type of treatment desired, as well as on the body mass of the patient. The active compound may, of course, be administered on its own or in the form of an appropriate medicinal composition containing, for instance, an appropriate pharmaceutical carrier or diluent. Other substances can, of course, also be employed in such medicinal compositions, such as antioxidants and stabilisers, the use of which is well known to persons skilled in the art. In a treatment of psoriasis, the active compound will, typically, be formulated for topical application to the patient, for instance in the form of ointment, cream or lotion. It is believed that the compounds described herein, can also be used in a vaccine preparation as an adjuvant, in situations where enhanced Th2 responses would be beneficial, for example when vaccinating against worm infection in humans and domestic animals.

EXAMPLES OF COMPOUNDS OF THE FORMULA I

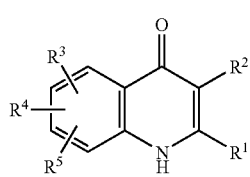

(I)

| Compound No. | $R^1$ | $R^2$ | $R^3$ | $R^4$ | $R^5$ |
|---|---|---|---|---|---|
| 1 | $(CH_2)_2CH_3$ | OH | H | H | H |
| 2 | $(CH_2)_4CH_3$ | OH | H | H | H |
| 3 | $(CH_2)_6CH_3$ | OH | H | H | H |
| 4 | $(CH_2)_8CH_3$ | OH | H | H | H |
| 5 | $(CH_2)_{10}CH_3$ | OH | H | H | H |
| 6 | $(CH_2)_6COOH$ | OH | H | H | H |
| 7 | $(CH_2)_6CH_3$ | H | H | H | H |
| 8 | $(CH_2)_6CH_3$ | CHO | H | H | H |
| 9 | $(CH_2)_6CH_3$ | Cl | H | H | H |
| 10 | $(CH_2)_6CH_3$ | COOH | H | H | H |
| 11 | $(CH_2)_6CH_3$ | $CONH_2$ | H | H | H |
| 12 | $(CH_2)_6CH_3$ | $CONHCH_3$ | H | H | H |
| 13 | $(CH_2)_6CH_3$ | OH | 6-Me | H | H |
| 14 | $(CH_2)_6CH_3$ | OH | 7-Me | H | H |
| 15 | $(CH_2)_6CH_3$ | OH | 6-OMe | H | H |
| 16 | $(CH_2)_6CH_3$ | OH | 7-OMe | H | H |
| 17 | $(CH_2)_6CH_3$ | OH | 6-Me | 7-Me | H |
| 18 | $(CH_2)_6CH_3$ | OH | 6-OMe | 7-OMe | H |

EXPERIMENTAL

Synthesis of 2-heptyl-3-hydroxy-4(1H)-quinolone

Preparation of 5-octanoyl Meldrum's Acid (2,2-dimethyl-5-octanoyl-1,3-dioxane-4,6-dione)

N,N'-Dicyclohexylcarbodiimide (11 mmol) was added to a stirred solution of octanoic acid (10 mmol) and 4-dimethylaminopyridine (12 mmol) in dry dichloromethane (40 ml). The mixture was stirred at room temperature for 1 hour and Meldrum's acid (10 mmol) was added. The stirring was continued at room temperature overnight. The solvent was removed in vacuum and the residue redissolved in ethyl acetate and filtered. The filtrate was washed with 2 M HCl solution and dried over $MgSO_4$. The solvent was rotary evaporated to obtain the title product as an oil in 95% yield and was used without purification in the next step.

Preparation of Ethyl 3-oxodecanoate

A solution of 5-octanoyl Meldrum's acid (10 mmol) in dry ethanol (50 ml) was heated under reflux for 4 hours. The solvent was evaporated in vacuum and the residue redissolved in ethyl acetate. The solution was sequentially washed with a saturated solution of sodium bicarbonate, 1 M $KHSO_4$ and finally brine. Drying ($MgSO_4$) and concentration in vacuum afforded the title β-keto ester as an oil in nearly quantitative yield.

$^1$H NMR (90 MHz, $CDCl_3$) δ 0.9 (3H, t, $CH_3$), 1.3 (11H, m, $OCH_2CH_3$ and $CH_3(CH_2)_4$), 1.6 (2H, m, $CH_2CH_2CO$), 2.5 (2H, t, $CH_2CO$), 3.4 (2H, s, $COCH_2CO$), 4.2 (3H, q, $OCH_2$).

Preparation of Ethyl 3-anilino-2-decenoate

A solution of aniline (6 mmol), ethyl 3-oxodecanoate (6 mmol) and toluene-p-sulfonic acid (50 mg) in dry toluene (60 ml) was heated under reflux for 24 hours using Dean-Stark apparatus for the azeotropic removal of water. The solvent was removed in vacuum to afford the title product as an oil which was used without purification in the next step.

Preparation of 2-heptyl-4(1H)-quinolone

The crude product of ethyl 3-anilino-2-decenoate was mixed with diphenyl ether (50 ml) and heated under reflux for 30 minutes. The solution was cooled to room temperature and then diluted with petroleum ether (b.p. 60-80° C.; 200 ml). The mixture was stirred and the petroleum ether decanted off. The product was chromatographed on a silica column using 3% $MeOH/CH_2Cl_2$ as the mobile phase. 2-Heptyl-4(1H)-quinolone was obtained as a crystalline solid in 50% yield.

$^1$H NMR (90 MHz, $CDCl_3$) δ 0.8 (3H, t, $CH_3$), 1.2 (8H, m, $CH_3(CH_2)_4$), 1.7 (2H, m, $NHCCH_2CH_2$), 2.7 (2H, m, $NHCCH_2$), 6.2 (1H, s, 3-H), 7.3 (1H, m, 6-H), 7.6 (1H, m, 7-H), 7.8 (1H, d, 5-H), 8.4 (1H, d, 8-H), 12.7 (1H, br s, NH).

Preparation of 3-formyl-2-heptyl-4(1/H)-quinolone

A mixture of 2-heptyl-4(1H)-quinolone (5 mmol), hexamine (2.5 mmol), and TFA (7.5 ml) was stirred at reflux under nitrogen for 30 hours. MeOH (15 ml) and water (15 ml) were added, and heating was continued for 1 hour. 3 M HCl (5 ml) was added and the heating was continued for a further period of 30 minutes. The mixture was cooled and the precipitate removed by filtration and washed with water. The solid on trituration with acetone afforded the title compound in 40% yield. Recrystallisation from MeOH/EtOAc gave colourless needles, mp 245-248° C. (dec).

¹H NMR (250 MHz, DMSO-d₆) δ 0.82 (3H, t, CH₃), 1.27 (8H, m, CH₃(CH₂)₄), 1.6 (2H, m, NHCCH₂CH₂), 3.0 (2H, m, NHCCH₂), 7.38 (1H, dd, 6-H), 7.57 (1H, d, 7-H), 7.70 (1H, dd, 5-H), 8.12 (1H, d, 8-H), 10.37 (1H, s, CHO), 12.12 (1H, br s, NH).

Preparation of 2-heptyl-3-hydroxy-4(1/H)-quinolone

Aqueous hydrogen peroxide (27.5 wt % solution in water, 145 μl) was added to a solution of 3-formyl-2-heptyl-4(1H)-quinolone (1 mmol) in EtOH (3 ml) and 1M NaOH solution (1.0 ml) under nitrogen, and the mixture was stirred at room temperature for 6 hours. The precipitate was removed by filtration, air dried and crystallised from EtOAc to give 2-heptyl-3-hydroxy-4(IH-quinolone in 70% yield as off-white needles, mp 195-197° C.

¹H NMR (250 MHz, DMSO-d₆) δ 0.82 (3H, t, CH₃) 1.27 (8H, m, CH₃(CH₂)₄), 1.63 (2H, m, NHCCH₂CH₂), 2.72 (2H, m, NHCCH₂), 7.20 (1H, m, 6,7-H₂), 7.52 (2H, m, 5-H), 8.00 (1H, br s, OH), 8.08 (1H, d, 8-H), 11.44 (1H, br s, NH).

Immunomodulatory Activity of
2-heptyl-3-hydroxy-4(1H)-quinolone

Materials and Methods

1. ConA Mitogen-Stimulated Proliferation of Murine Splenocytes

The concanavalin A (ConA) cell proliferation assay was used to assess the effect of the title compound on T-cell activation and proliferation. Proliferation was assessed by the incorporation of [³H]-thymidine into DNA. Eight-week-old female BALB/c mice were obtained from Harlan (Bicester, Oxon, UK) and given food and water ad libitum. Splenocyte suspensions were prepared by removing the spleens and placing them into RPMI 1640 medium. The spleens were forced through 70 μm pore size wire gauzes using the plunger from a 5 ml syringe to produce a single cell suspension. The cells were pelleted by centrifugation, and erythrocytes were lysed with 0.017M Tris, 0.144M ammonium chloride buffer, pH 7.2. Leucocytes were washed twice with RPMI 1640 medium with 2% (vol/vol) foetal calf serum (FCS) and resuspended in complete cell culture medium (CTCM) consisting of RPMI 1640 medium with 5% FCS, 2 mM L-glutamine, and 5×10−5 M 2-mercaptoethanol. The title compound was tested at doubling down dilutions ranging from about 10 to 0.2 μM in a final volume of 200 μl of CTCM, containing ConA (Sigma, Poole, UK) at 1 μg/ml and 100,000 spleen cells. Following incubation for 48 h at 37° C. in 5% CO₂-air, 0.25 μCi [³H]-thymidine (Amersham) in 10 μl volume made up in RPMI 1640 medium was added and the cells were incubated for a further 24 h. Cells were harvested onto fibreglass filters with a Packard filtermate harvester. After the addition of 25 μl of MicroScint-O (Packard) to each well the filters were counted with the Packard TopCount scintillation counter.

Mitogen (Concanavalin A) induced murine splenocyte proliferation was indicated by the incorporation of tritated thymidine into the DNA in the mouse spleen cells as shown by counts per minute using the scintillation counter. The inhibitory effect of the title compound being tested on cell proliferation was indicated by a reduction in counts per minute. FIG. 1 shows the plots of counts per minute (cpm) against the concentrations (micromolar) of the title compound and the vehicle dimethylsulphoxide (DMSO). It can be seen, from this figure, that 2-heptyl-3-hydroxy-4(1H)quinolone inhibits splenocyte proliferation.

2.

Figure 2:
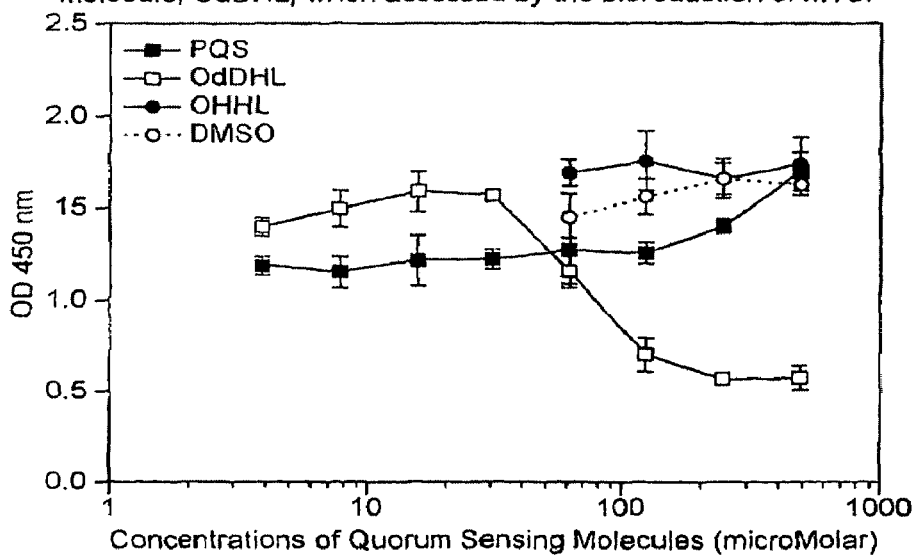

The human monocytic cell line, Mono Mac 6, was treated with concentrations of bacterial quorum sensing molecules 2-heptyl-3-hydroxy-4(1H)quinolone (PQS), N-(3-oxododecanoyl)-L-homoserine lactone (OdDHL) and N-(3-oxohexanoyl)-L-homoserine lactone. Cells at 100,000 per well were exposed to quorum sensing molecules ranging from 3.90625 to 500 μM after which the cells were stimulated with 10 ng/ml *E. coli* LPS and 5 ng/ml phorbol-myristrate acetate to induce the overnight release of TNF-α into the culture media. A tetrazolium compound (3-(4,5-dimethylthazol-2-yl)-5-(3-carboxymethoxyphenyl)-2-(4-sulfophenyl)-2H-tetrazolium, inner salt MTS was added to the cells to determine cellular viability after treatment with the quorum sensing molecules. MTS is bioreduced by cells into a formazan product that is soluble in tissue culture medium. The production of formazan was determined by measuring the absorbance of the compound at 450 nm. The results are shown in FIG. 2. A titration of cell numbers was included to correlate to the number of viability cells in the treated wells as set out in the table below.

|   | 1 | 2 | 3 | 4 | 5 | 6 | 7 | 8 | 9 | 10 | 11 | 12 |
|---|---|---|---|---|---|---|---|---|---|----|----|----|
| A | 100,000 | cells | | 500 | μM | PQS | 500 | μM | OdDHL | 500 | μM | OHHL |
| B | 50,000 | | | 250 | | | 250 | | | 250 | | |
| C | 25,000 | | | 125 | | | 125 | | | 125 | | |
| D | 12,500 | | | 62.5 | | | 62.5 | | | 62.5 | | |
| E | 6,250 | | | 31.25 | | | 31.25 | | | 1:200 | dilution | DMSO |
| F | 3,125 | | | 15.625 | | | 15.625 | | | 1:400 | | |
| G | 1,563 | | | 7.8125 | | | 7.8125 | | | 1:800 | | |
| H | Culture | Medium | alone | 3.90625 | | | 3.90625 | | | 1:1,600 | | |

Figure 3:
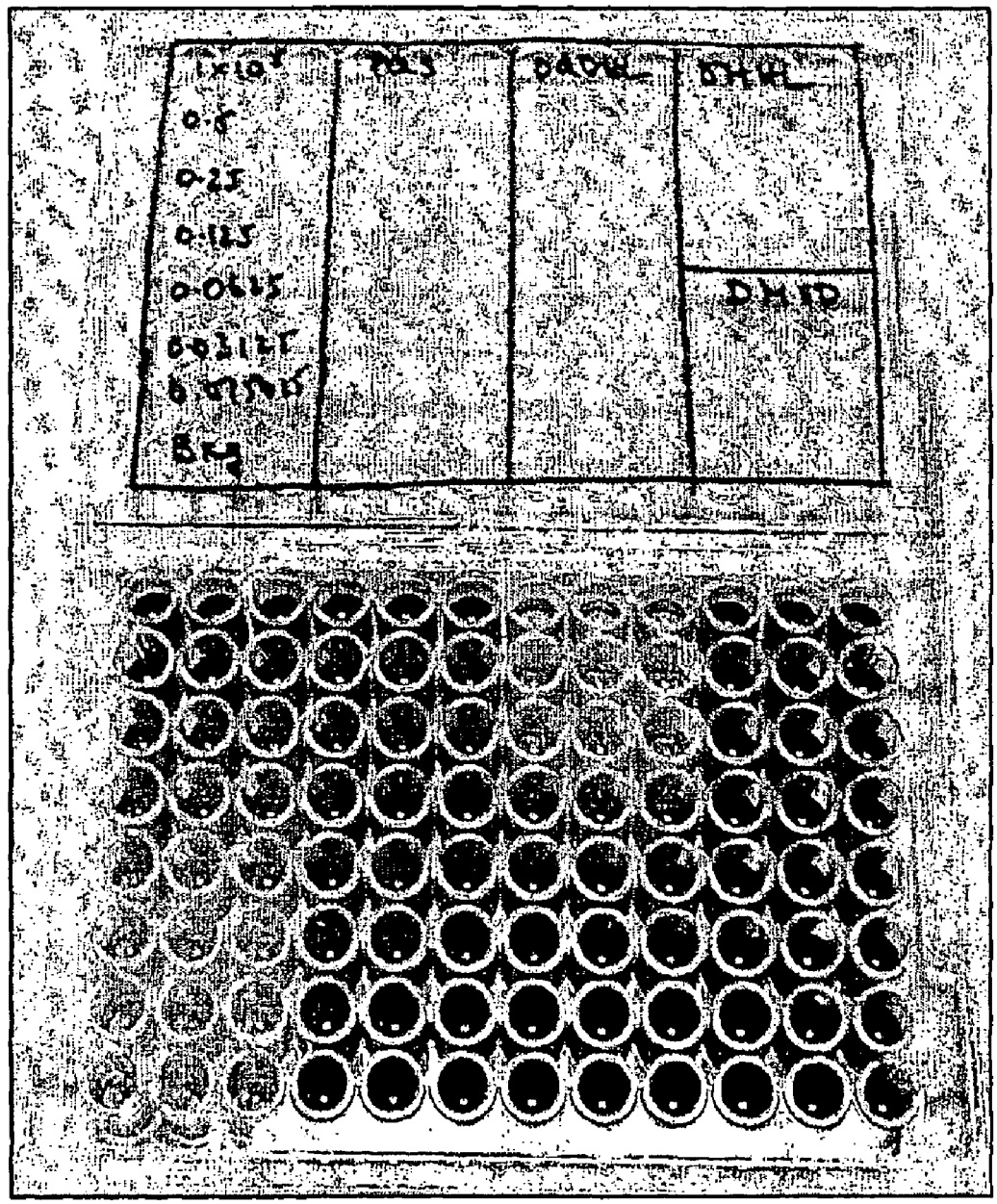

The photograph (FIG. 3) shows the production of formazan due to bioreducibility of Mono Mac 6 cells (at 100,000 cells per well) after their overnight exposure to bacterial quorum sensing molecules.

3.

(A) In Vitro Proliferation Assays and the Release of IL-2

Figure 4:
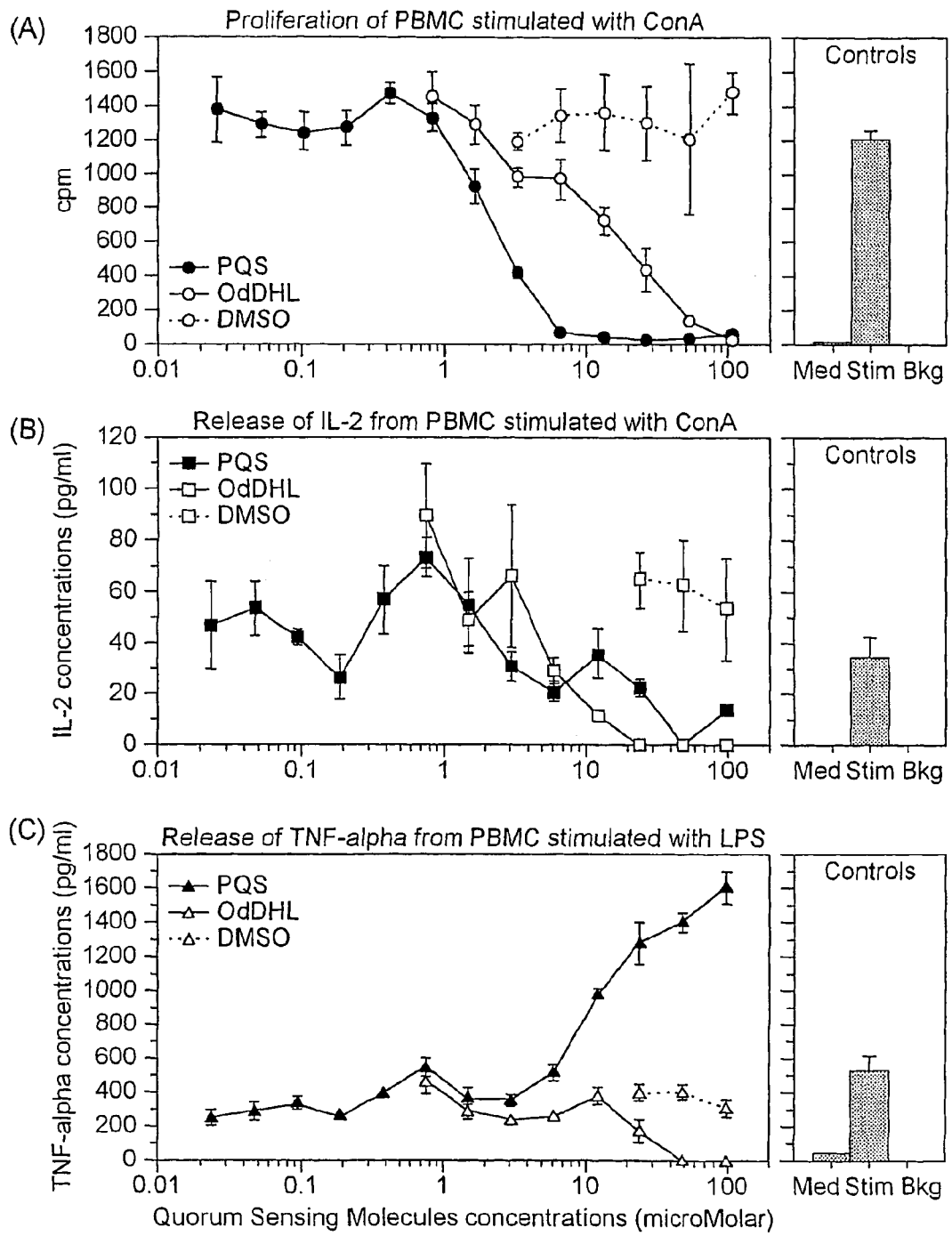

Human peripheral blood mononuclear cells (PBMC) were isolated from heparinised whole blood by buoyant density centrifugation over Histopague 1077 (Sigma, Poole, UK) 600 g for 20 minutes. PBMC harvested from the 'buffy' layers were washed and then aliquoted into 96-well plates at 100,000 per well. PBMC were exposed to bacterial quorum sensing molecules (PQS or OdDHL) at concentrations ranging from 0.78125 to 100 μM and then stimulated with 1 μg/ml of Concanavalin A (ConA). After an overnight culture 50 μl of the culture supernatant was removed for the detection of IL-2 released by 'sandwich' ELISA. The cells were returned to culture for another 24 hours before 0.25 μCi per well of $^3$H-thymidine was added. Following an 18-hour pulse the human PBMC were harvested onto fibreglass filters which were then counted in the presence of MicroScint-O with the Packard TopCount scintillation counter. Results are shown in FIG. 4A.

(B) Human IL-2 'Sandwich' ELISA

Human leucocytes when stimulated with ConA released the cytokine IL-2. The levels of cytokine produced in the culture supernatants after 24 h were determined in a 'sandwich' ELISA. Briefly, 96-well Nunc MaxiSorp (Life Technologies, Paisley, UK) plates were coated with 50 μl of a 'capture' anti-IL-2 monoclonal antibody (BD Pharmingen, UK) in 0.05 M carbonate/bicarbonate buffer, pH 9.6 overnight at 4° C. After washing the plates three times with PBS-Tween, which contained phosphate buffered saline (PBS) with 0.5% (vol/vol) Tween 20 (Sigma, Poole, UK), the plates were blocked with 1% (wt/vol) bovine serum albumin (BSA) (Sigma, Poole, UK) at room temperature for 2 h. Following three washes with PBS-Tween, 50 μl of cell culture supernatants were added and incubated overnight at 4° C.; standard human IL-2 (BD Pharmingen, UK) were included for each plate. After four washes with PBS-Tween, 50 μl of a biotinylated anti-IL-2 monoclonal antibody (BD Pharmingen, UK) was added diluted in 1% BSA in PBS-Tween and incubated at room temperature for 1 h. Following four washes, the bound biotinylated antibody was detected with 50 μl of a 1:1,000 dilution of Streptavidin-peroxidase (BD Pharmingen, UK). At the end of an hour incubation at room temperature, the plates were thoroughly washed six times with PBS-Tween and the assay was developed by the addition of 100 μl of 0.1 mg/ml of tetramethyl benzidine substrate (Sigma, Poole, UK) in 0.1 M sodium acetate buffer, pH 6 containing 0.03% $H_2O_2$. The enzyme reaction was stopped with 50 μl of 2.5 M $H_2SO_4$ after a development of 10 minutes at room temperature and the development was read at 450 nm with a spectrophotometric 96-well plate reader. Results are shown in FIG. 4B.

(C) In Vitro Stimulation of Human PBMC for the Release of TNF-α

Human PBMC, at 100,000 cell per well, were stimulated with $1 \times 10^{-5}$ μg/ml LPS E. coli strain 055:B5. Following culture for 24 hours the cell culture supernatants were collected and tested for TNF-α levels by 'sandwich' ELISA similarly described above for the IL-2 detection assay. Results are shown in FIG. 4C.

DISCUSSION

The data presented indicate that two chemically distinct bacterial quorum sensing molecules modulate immune responses differentially. OdDHL inhibits human PBMC cell proliferation, IL-2 secretion and TNF-α production whereas PQS has no effect on TNF-α production at low dose, and may enhance TNF-α production at high dose. Furthermore, PQS has no effect on cell viability, as adjudged by MTS conversion, in contrast to OdDHL.

What is claimed is:

1. A method of suppressing T-cell proliferation in a living animal body by
administering to the living animal body a therapeutically-effective amount of a compound of the formula I

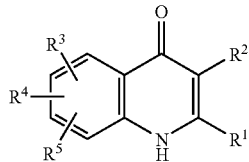

(I)

wherein R1 is a straight or branched chain, saturated or ethylenically-unsaturated aliphatic hydrocarbyl group containing from 1 to 18 carbon atoms which may optionally be substituted by one or more substituent groups selected from halo, 1-6C alkoxy, carboxy, 1-6C alkoxycarbonyl and NR$^6$R$^7$, wherein each of R$^6$ and R$^7$ is independently selected from H and 1-6C alkyl or R$^6$ and R$^7$ together with the N atom to which they are attached form a saturated heterocyclic group selected from piperidino, piperazino and morpholin; R$^2$ is group selected from H, —OH, halo, —CHO, —CO$_2$H and CONHR$^8$ wherein R$^8$ is H or a 1-6C alkyl; each of R$^3$, R$^4$ and R$^5$ is independently selected from H, —CH$_3$, —OCH$_3$ and halo; or a non-toxic pharmaceutically-acceptable salt thereof; wherein said suppression of T-cell proliferation treats autoimmune diseases.

2. The method according to claim 1, wherein the compound has the formula I in which R$^1$ is a straight chain alkyl group having from 3 to 13 carbon atoms.

3. The method according to claim 2, wherein R$^1$ is n-heptyl.

4. The method according to claim 1, wherein R$^2$ is OH.

5. The method according to claim 4, wherein the compound of the formula I is 2-n-heptyl-3-hydroxy-4 (1 H)-quinolone.

6. The method according to claim 1, wherein the autoimmune disease is selected from the group consisting of psoriasis, multiple sclerosis and rheumatoid arthritis.

7. A method of treating an individual with psoriasis, said method comprising:
applying topically to the individual a therapeutically-effective amount of an active compound to suppress T-cell proliferation at the site of topical application. wherein the active compound is formulated in a medicament for topical application and has the formula I

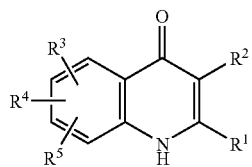

wherein $R^1$ is a straight or branched chain, saturated or ethylenically-unsaturated aliphatic hydrocarbyl group containing from 1 to 18 carbon atoms which may optionally be substituted by one or more substituent groups selected from halo, 1-6C alkoxy, carboxy, 1-6C alkoxy-carbonyl and $NR^6R^7$, wherein each of $R^6$ and $R^7$ is independently selected from H and 1-6C alkyl or $R^6$ and $R^7$ together with the N atom to which they are attached form a saturated heterocyclic group selected from piperidino, piperazino and morpholino; $R^2$ is group selected from H, —OH, halo, —CHO, —$CO_2H$ and $CONHR^8$ wherein $R^8$ is H or a 1-6C akyl; each of $R^3$, $R^4$ and $R^5$ is independently selected from H, —$CH_3$, —$OCH_3$ and halo; or a non-toxic pharmaceutically-acceptable salt thereof.

8. The method of claim 1, wherein the medicament is an ointment, cream or lotion.

9. The method of claim 7, wherein the active compound is 2-n-heptyl-3-hydroxy-4(1H)-quinolone.

* * * * *